United States Patent [19]

Nelson

[11] Patent Number: 5,942,014
[45] Date of Patent: Aug. 24, 1999

[54] PYRIDYL AND PIPERIDYL ESTERS OF POLYALKLPHENOXYALKANOLS AND FUEL COMPOSITIONS CONTAINING THE SAME

[75] Inventor: Kenneth D. Nelson, Clearlake, Calif.

[73] Assignee: Chevron Chemical Company LLC, San Francisco, Calif.

[21] Appl. No.: 09/141,997

[22] Filed: Aug. 28, 1998

[51] Int. Cl.⁶ ............ C10L 1/22; C07D 211/60; C07D 211/62; C07D 211/04
[52] U.S. Cl. .......... 44/333; 546/227; 546/322; 546/326
[58] Field of Search ............ 44/333; 546/227, 546/322, 326

[56] References Cited

U.S. PATENT DOCUMENTS

| | | | |
|---|---|---|---|
| 2,714,607 | 8/1955 | Matter | 260/471 |
| 3,149,933 | 9/1964 | Ley et al. | 44/75 |
| 3,285,855 | 11/1966 | Dexter et al. | 252/57 |
| 3,303,198 | 2/1967 | Suter et al. | 546/227 |
| 3,330,859 | 7/1967 | Dexter et al. | 560/473 |
| 3,434,814 | 3/1969 | Dubeck et al. | 44/69 |
| 3,849,085 | 11/1974 | Kruez et al. | 44/78 |
| 4,134,846 | 1/1979 | Machleder et al. | 252/51.5 |
| 4,320,021 | 3/1982 | Lange | 252/51.5 |
| 4,328,322 | 5/1982 | Baron | 521/163 |
| 4,347,148 | 8/1982 | Davis | 252/51.5 |
| 4,386,939 | 6/1983 | Lange | 44/63 |
| 4,859,210 | 8/1989 | Franz et al. | 44/53 |
| 5,090,914 | 2/1992 | Reardan et al. | 435/188 |
| 5,196,142 | 3/1993 | Mellet et al. | 252/311 |
| 5,211,721 | 5/1993 | Sung et al. | 44/389 |
| 5,380,345 | 1/1995 | Cherpeck | 44/399 |
| 5,407,452 | 4/1995 | Cherpeck | 44/323 |
| 5,427,591 | 6/1995 | Cherpeck | 44/400 |
| 5,618,320 | 4/1997 | Cherpeck | 44/399 |
| 5,755,833 | 5/1998 | Ishida et al. | 44/333 |
| 5,837,016 | 11/1998 | Ishida et al. | 44/333 |
| 5,837,867 | 11/1998 | Ishida et al. | 44/333 |

*Primary Examiner*—Jerry D. Johnson
*Attorney, Agent, or Firm*—Steven G. K. Lee

[57] ABSTRACT

Pyridyl and piperidyl esters of polyalkylphenoxyalkanols having the formula:

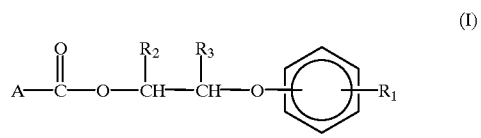

(I)

or a fuel soluble salt thereof, wherein A is selected from the group consisting of 3-pyridyl, 4-pyridyl, 3-piperidyl, and 4-piperidyl;

$R_1$ is a polyalkyl group having an average molecular weight in the range of from about 450 to 5,000; and $R_2$ and $R_3$ are independently hydrogen or lower alkyl having from about 1 to 6 carbon atoms.

The compounds of formula I are useful as fuel additives for the prevention and control of engine deposits.

39 Claims, No Drawings

PYRIDYL AND PIPERIDYL ESTERS OF POLYALKLPHENOXYALKANOLS AND FUEL COMPOSITIONS CONTAINING THE SAME

BACKGROUND OF THE INVENTION

1. Field of the Invention

This invention relates to novel pyridyl and piperidyl esters of polyalkylphenoxyalkanols and derivatives thereof. In a further aspect, this invention relates to the use of these compounds in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amounts of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., disclose a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Amino phenols are also known to function as detergents/dispersants, antioxidants and anti-corrosion agents when used in fuel compositions. U.S. Pat. No. 4,320,021, issued Mar. 16, 1982 to R. M. Lange, for example, discloses amino phenols having at least one substantially saturated hydrocarbon-based substituent of at least 30 carbon atoms. The amino phenols of this patent are taught to impart useful and desirable properties to oil-based lubricants and normally liquid fuels.

Similarly, U.S. Pat. No. 3,149,933, issued Sep. 22, 1964 to K. Ley et al., disclose hydrocarbon-substituted amino phenols as stabilizers for liquid fuels. U.S. Pat. No. 4,386,939, issued Jun. 7, 1983 to R. M. Lange, discloses nitrogen-containing compositions prepared by reacting an amino phenol with at last one 3- or 4-membered ring heterocyclic compound in which the hetero atom is a single oxygen, sulfur or nitrogen atom, such as ethylene oxide. The nitrogen-containing compositions of this patent are taught to be useful as additives for lubricants and fuels.

Nitro phenols have also been employed as fuel additives. For example, U.S. Pat. No. 4,347,148, issued Aug, 31, 1982 to K. E. Davis, discloses nitro phenols containing at least one aliphatic substituent having at least about 40 carbon atoms. The nitro phenols of this patent are taught to be useful as detergents, dispersants, antioxidants and demulsifiers for lubricating oil and fuel compositions.

Similarly, U.S. Pat. No. 3,434,814, issued Mar. 25, 1969 to M. Dubeck et al., disclose a liquid hydrocarbon fuel composition containing a major quantity of a liquid hydrocarbon of the gasoline boiling range and a minor amount sufficient to reduce exhaust emissions and engine deposits of an aromatic nitro compound having an alkyl, aryl, aralkyl, alkanoyloxy, alkoxy, hydroxy or halogen substituent.

More recently, certain poly(oxyalkylene) esters have been shown to reduce engine deposits when used in fuel compositions. U.S. Pat. No. 5,211,721, issued May 18, 1993 to R. L. Sung et al., for example, disclose an oil soluble polyether additive comprising the reaction product of a polyether polyol with an acid represented by the formula RCOOH in which R is a hydrocarbyl radical having 6 to 27 carbon atoms. The poly(oxyalkylene) ester compounds of this patent are taught to be useful for inhibiting carbonaceous deposit formation, motor fuel hazing, and as ORI inhibitors when employed as soluble additives in motor fuel compositions.

Poly(oxyalkylene) esters of amino- and nitrobenzoic acids are also known in the art. For example, U.S. Pat. No. 2,714,607, issued Aug. 2, 1955 to M. Matter, discloses polyethoxy esters of aminobenzoic acids, nitrobenzoic acids and other isocyclic acids. These polyethoxy esters are taught to have excellent pharmacological properties and to be useful as anesthetics, spasmolytics, analeptics, and bacteriostatics.

Similarly, U.S. Pat. No. 5,090,914, issued Feb. 25, 1992 to D. T. Reardan et al., disclose poly(oxyalkylene) aromatic compounds having an amino or hydrazinocarbonyl substituent on the aromatic moiety and an ester, amide, carbamate, urea or ether linking group between the aromatic moiety and the poly(oxyalkylene) moiety. These compounds are taught to be useful for modifying macromolecular species such as proteins and enzymes.

U.S. Pat. No. 4,328,322, issued Sep. 22, 1980 to R. C. Baron, discloses amino- and nitrobenzoate esters of oligomeric polyols, such as poly(ethylene) glycol. These materials are used in the production of synthetic polymers by reaction with a polyisocyanate.

U.S. Pat. No. 4,859,210, issued Aug. 22, 1989 to Franz et al., disclose fuel compositions containing (1) one or more polybutyl or polyisobutyl alcohols wherein the polybutyl or polyisobutyl group has a number average molecular weight of 324 to 3,000, or (2) a poly(alkoxylate) of the polybutyl or polyisobutyl alcohol, or (3) a carboxylate ester of the polybutyl or polyisobutyl alcohol. This patent further teaches that when the fuel composition contains an ester of a polybutyl or polyisobutyl alcohol, the ester-forming acid group may be derived from saturated or unsaturated, aliphatic or aromatic, acyclic or cyclic mono- or polycarboxylic acids.

U.S. Pat. Nos. 3,285,855, and 3,330,859 issued Nov. 15, 1966 and Jul. 11, 1967, respectively, to Dexter et al., disclose alkyl esters of dialkyl hydroxybenzoic and hydroxyphenylalkanoic acids wherein the ester moiety contains from 6 to 30 carbon atoms. These patents teach that such esters are useful for stabilizing polypropylene and other organic material normally subject to oxidative deterioration. Similar alkyl esters containing hindered dialkyl hydroxyphenyl groups are disclosed in U.S. Pat. No. 5,196,565, which issued Mar. 23, 1993 to Ross.

U.S. Pat. No. 5,196,142, issued Mar. 23, 1993 to Mollet et al., disclose alkyl esters of hydroxyphenyl carboxylic acids wherein the ester moiety may contain up to 23 carbon atoms. This patent teaches that such compounds are useful as antioxidants for stabilizing emulsion-polymerized polymers.

U.S. Pat. No. 5,407,452, issued Apr. 18, 1995, and corresponding International Application Publication No. WO 95/04118, published Feb. 9, 1995, disclose certain poly (oxyalkylene) nitro and aminoaromatic esters having from 5 to 100 oxyalkylene units and teach the use of such compounds as fuel additives for the prevention and control of engine deposits.

Similarly, U.S. Pat. No. 5,427,591, issued Jun. 27, 1995, and corresponding International Application Publication No. WO 94/14926, published Jul. 7, 1994, disclose certain poly(oxyalkylene) hydroxyaromatic esters which are useful as fuel additives to control engine deposits.

In addition, U.S. Pat. No. 5,380,345, issued Jan. 10, 1995, and corresponding International Application Publication No. WO 95/15366, published Jun. 8, 1995, disclose certain polyalkyl nitro and aminoaromatic esters useful as deposit control additives for fuels. Moreover, prior International Application Publication No. WO 95/11955, published May 4, 1995, discloses certain polyalkyl hydroxyaromatic esters that are also useful as deposit control fuel additives. More recently, U.S. Pat. No. 5,618,320, issued Apr. 8, 1997, further discloses aromatic esters of polyalkylphenoxyalkanols that provide excellent control of engine deposits, especially intake valve deposits, when employed as fuel additives in fuel compositions.

SUMMARY OF THE INVENTION

I have now discovered certain pyridyl and piperidyl esters of polyalkylphenoxyalkanols, which provide excellent control of engine deposits, especially intake valve deposits, when employed as fuel additives in fuel compositions.

The compounds of the present invention include those having the following formula and fuel soluble salts thereof:

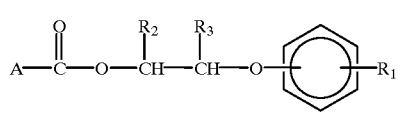

(I)

wherein A is selected from the group consisting of 3-pyridyl, 4-pyridyl, 3-piperidyl, and 4-piperidyl;

$R_1$ is a polyalkyl group having an average molecular weight in the range of from about 450 to 5,000; and $R_2$ and $R_3$ are independently hydrogen or lower alkyl having from about 1 to 6 carbon atoms.

The present invention further provides a fuel composition comprising a major amount of hydrocarbons boiling in the gasoline or diesel range and a deposit-controlling effective amount of a compound of the present invention.

The present invention additionally provides a fuel concentrate comprising an inert stable oleophilic organic solvent boiling in the range of from about 150° F. to 400° F. and from about 10 to 70 weight percent of a compound of the present invention.

Among other factors, the present invention is based on the surprising discovery that certain pyridyl and piperidyl esters of polyalkylphenoxyalkanols provide excellent control of engine deposits, especially on intake valves, when employed as additives in fuel compositions.

DETAILED DESCRIPTION OF THE INVENTION

Based on performance (e.g. deposit control), the preferred compounds of the invention are those wherein A is preferably 4-pyridyl or 4-piperidyl. Most preferably, A is 4-piperidyl.

Preferably, $R_1$ is a polyalkyl group having an average molecular weight in the range of from about 500 to 3,000, more preferably about 700 to 3,000, and most preferably about 900 to 2,500. It is preferred that the $R_1$ substituent on the phenyl ring is located para or meta, more preferably para, relative to the ether linking group.

Preferably, one of $R_2$ and $R_3$ is hydrogen or lower alkyl of from about 1 to 4 carbon atoms, and the other is hydrogen. More preferably, one of $R_2$ and $R_3$ is hydrogen, methyl or ethyl, and the other is hydrogen. Most preferably, $R_2$ is hydrogen, methyl or ethyl, and $R_3$ is hydrogen.

The compounds of the present invention will generally have a sufficient molecular weight so as to be non-volatile at normal engine intake valve operating temperatures (from about 200° C. to 250° C.). Typically, the molecular weight of the compounds of this invention will range from about 700 to 3,500, preferably from about 700 to 2,500.

Fuel-soluble salts of the compounds of formula I can be readily prepared and such salts are contemplated to be useful for preventing or controlling engine deposits. Suitable salts include, for example, those obtained by protonating the nitrogen atom on the pyridyl or piperidyl ring with a strong organic acid, such as an alkyl or arylsulfonic acid. Preferred salts are derived from toluenesulfonic acid and methanesulfonic acid.

DEFINITIONS

As used herein, the following terms have the following meanings unless expressly stated to the contrary.

The term "polyalkyl" refers to an alkyl group which is generally derived from polyolefins which are polymers or copolymers of mono-olefins, particularly 1-mono-olefins, such as ethylene, propylene, butylene, and the like. Preferably, the mono-olefin employed will have from about 2 to 24 carbon atoms, and more preferably, about 3 to 12 carbon atoms. More preferred mono-olefins include propylene, butylene, particularly isobutylene, 1-octene, and 1-decene.

Polyolefins prepared from such mono-olefins include polypropylene, polybutene, especially polyisobutene, and the polyalphaolefins produced from 1-octene and 1-decene.

The term "pyridyl" refers to the radical —$C_5H_4N$ from pyridine.

The term "piperidyl" refers to the radical —$C_5H_{10}NH$ from piperidine.

The term "fuel" or "hydrocarbon fuel" refers to normally liquid hydrocarbons having boiling points in the range of gasoline and diesel fuels.

General Synthetic Procedures

The pyridyl and piperidyl esters of the polyalkylphenoxyalkanols of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

Synthesis

The pyridyl esters of polyalkylphenoxyalkanols of the present invention may be prepared by a process which initially involves hydroxyalkylation of a polyalkylphenol of the formula:

(II)

wherein $R_1$ is as defined above, with an alkylene carbonate of the formula:

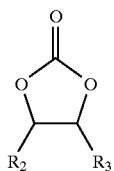
(III)

wherein $R_2$ and $R_3$ are as defined above, in the presence of a catalytic amount of an alkali metal hydride or hydroxide, or alkali metal salt, to provide a polyalkylphenoxyalkanol of the formula:

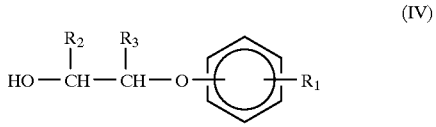
(IV)

wherein $R_1$, $R_2$, and $R_3$ are as defined above.

The polyalkylphenols of formula II are well known materials and are typically prepared by the alkylation of phenol with the desired polyolefin or chlorinated polyolefin. A further discussion of polyalkylphenols can be found, for example, in U.S. Pat. Nos. 4,744,921 and 5,300,701.

Accordingly, the polyalkylphenols of formula II may be prepared from the corresponding olefins by conventional procedures. For example, the polyalkylphenols of formula II above may be prepared by reacting the appropriate olefin or olefin mixture with phenol in the presence of an alkylating catalyst at a temperature of from about 25° C. to 150° C., and preferably about 30° C. to 100° C. either neat or in an essentially inert solvent at atmospheric pressure. A preferred alkylating catalyst is boron trifluoride. Molar ratios of reactants may be used. Alternatively, molar excesses of phenol can be employed, i.e., from about 2 to 3 equivalents of phenol for each equivalent of olefin with unreacted phenol recycled. The latter process maximizes monoalkylphenol. Examples of inert solvents include heptane, benzene, toluene, chlorobenzene, and 250 thinner which is a mixture of aromatics, paraffins and naphthenes.

The polyalkyl substituent on the polyalkylphenols employed in the invention is generally derived from polyolefins which are polymers or copolymers of mono-olefins, particularly 1-mono-olefins, such as ethylene, propylene, butylene, and the like. Preferably, the mono-olefin employed will have from about 2 to 24 carbon atoms, and more preferably, about 3 to 12 carbon atoms. More preferred mono-olefins include propylene, butylene, particularly isobutylene, 1-octene, and 1-decene. Polyolefins prepared from such mono-olefins include polypropylene, polybutene, especially polyisobutene, and the polyalphaolefins produced from 1-octene and 1-decene.

The preferred polyisobutenes used to prepare the presently employed polyalkylphenols are polyisobutenes, which comprise at least about 20% of the more reactive methylvinylidene isomer, preferably at least 50% and more preferably at least 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808. Such polyisobutenes, known as "reactive" polyisobutenes, yield high molecular weight alcohols in which the hydroxyl group is at or near the end of the hydrocarbon chain. Examples of suitable polyisobutenes having a high alkylvinylidene content include Ultravis 30, a polyisobutene having a number average molecular weight of about 1,300 and a methylvinylidene content of about 74%, and Ultravis 10, a polyisobutene having a number average molecular weight of about 950 and a methylvinylidene content of about 76%, both available from British Petroleum.

The alkylene carbonates of formula III are known compounds, which are available commercially or can be readily prepared using conventional procedures. Suitable alkylene carbonates include ethylene carbonate, propylene carbonate, 1,2-butylene carbonate, 2,3-butylene carbonate, and the like. A preferred alkylene carbonate is ethylene carbonate.

The catalyst employed in the reaction of the polyalkyphenol and alkylene carbonate may be any of the well-known hydroxyalkylation catalysts. Typical hydroxyalkylation catalysts include alkali metal hydrides, such as lithium hydride, sodium hydride and potassium hydride, alkali metal hydroxides, such as sodium hydroxide and potassium hydroxide, and alkali metal salts, for example, alkali metal halides, such as sodium chloride and potassium chloride, and alkali metal carbonates, such as sodium carbonate and potassium carbonate. The amount of catalyst employed will generally range from about 0.01 to 1.0 equivalent, preferably about 0.05 to 0.3 equivalent.

The polyalkylphenol and alkylene carbonate are generally reacted in essentially equivalent amounts in the presence of the hydroxyalkylation catalyst at a temperature in the range of from about 100° C. to 210° C., and preferably about 150° C. to 170° C. The reaction may take place in the presence or absence of an inert solvent.

The time of reaction will vary depending on the particular alkylphenol and alkylene carbonate reactants, the catalyst used and the reaction temperature. Generally, the reaction time will range from about 2 to 24 hours. The progress of the reaction is typically monitored by the evolution of carbon dioxide. At the completion of the reaction, the polyalkylphenoxyalkanol product is isolated using conventional techniques.

The hydroxyalkylation reaction of phenols with alkylene carbonates is well known in the art and is described, for example, in U.S. Pat. Nos. 2,987,555; 2,967,892; 3,283,030 and 4,341,905.

Alternatively, the polyalkylphenoxyalkanol product of formula IV may be prepared by reacting the polyalkylphenol of formula II with an alkylene oxide of the formula:

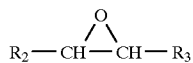
(V)

wherein $R_2$ and $R_3$ are as defined above, in the presence of a hydroxyalkylation catalyst as described above.

Suitable alkylene oxides of formula V include ethylene oxide, propylene oxide, 1,2-butylene oxide, 2,3-butylene oxide, and the like. A preferred alkylene oxide is ethylene oxide.

In a manner similar to the reaction with alkylene carbonate, the polyalkylphenol and alkylene oxide are reacted in essentially equivalent or equimolar amounts in the presence of from about 0.01 to 1.0 equivalent of a hydroxyalkylation catalyst, such as sodium or potassium hydride, at a temperature in the range of from about 30° C. to 150° C., for from about 2 to 24 hours. The reaction may be conducted in the presence or absence of a substantially anhydrous inert solvent. Suitable solvents include toluene, xylene, and the like. Generally, the reaction conducted at a pressure sufficient to contain the reactants and any solvent present, typically at atmospheric or higher pressure. Upon completion of the reaction, the polyalkylphenoxyalkanol is isolated by conventional procedures.

The polyalkylphenoxyalkanol of formula IV is subsequently reacted with a pyridyl acid of formula VI to provide the pyridyl ester compounds of formula I. This reaction can be represented as follows:

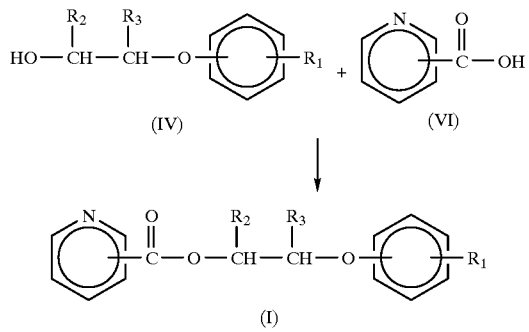

wherein A, $R_1$, $R_2$, and $R_3$ are as defined above.

This reaction is typically conducted by contacting a polyalkylphenoxyalkanol of formula IV with from about 0.25 to 1.5 molar equivalents of the pyridyl acid of formula VI in the presence of catalyst at a temperature in the range of from about 70 to 180° C. for from about 0.5 to 48 hours. Suitable acid catalysts for this reaction include p-toluenesulfonic acid, methanesulfonic acid, and the like. Optionally, the reaction can be conducted in the presence of an inert solvent, such as benzene, toluene, and the like. The water generated by this reaction is preferably removed during the course of the reaction, for example, by azeotropic distillation.

The pyridyl carboxylic acids of formula VI are known compounds and include nicotinic acid, and its isomer, 4-nicotinic acid.

The compounds of formula I also can be prepared by reacting the polyalkylphenoxyalkanol of formula IV with an acid halide of the pyridyl acid of formula VI such as an acid chloride or acid bromide. This can be represented by the following reaction equation:

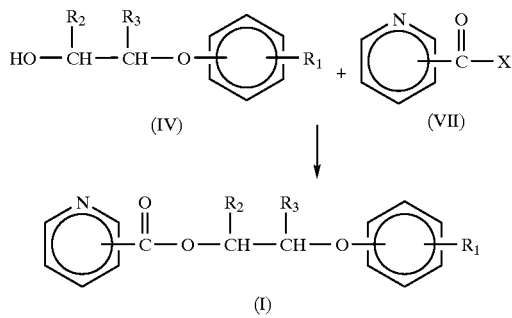

wherein X is halide, typically chloride or bromide, and A, $R_1$, $R_2$, and $R_3$ are as defined above.

Typically, this reaction is conducted by contacting the polyalkylphenoxyalkanol of formula IV with from about 0.9 to 1.5 molar equivalents of the acid halide of formula VII in an inert solvent, such as, for example, toluene, dichloromethane, diethyl ether, acetonitrile, and the like, at a temperature in the range of from about 25° C. to 150° C. The reaction is generally complete in from about 0.5 to 48 hours. Preferably, the reaction is conducted in the presence of a sufficient amount of an amine capable of neutralizing the acid generated during the reaction, such as, for example, triethylamine, di(isopropyl)ethylamine, pyridine, or 4-dimethylaminopyridine.

The acyl halides of formula VII can be prepared by contacting the corresponding pyridyl acid compound of formula VI with an inorganic acid halide, such as thionyl chloride, phosphorous trichloride, phosphorous tribromide, or phosphorous pentachloride; or with oxalyl chloride. Typically, this reaction will be conducted using from about 1 to 5 molar equivalents of the inorganic acid halide or oxalyl chloride, either neat or in an inert solvent, such as diethyl ether, at a temperature in the range of from about 20° C. to 80° C. for from about 1 to 48 hours. A catalyst, such as N,N-dimethylformamide, may also be used in this reaction. The pyridyl acyl halides may be isolated as the hydro halide salt. The salts can be used for the esterification directly by using an extra equivalent of base such as, for example, triethylamine, diisopropylethylamine, pyridine, or 4-dimethylaminopyridine.

In a similar fashion, compounds of formula I wherein the substituent A is a piperidyl group may be conveniently prepared by first preparing the corresponding pyridyl compound (i.e., where A is pyridyl), and then reducing the pyridyl group to a piperidyl group using conventional reducing conditions well known in the art. Hydrogenation of pyridyl groups is discussed in further detail in, for example, in P. N. Rylander, Catalytic Hydrogenation in Organic Synthesis, pp. 213–220, Academic Press (1979); and in M. Hudlicky, Reductions in Organic Chemistry, Second Edition, pp. 69–71, ACS monograph: 188, American Chemical Society (1996); and references cited therein.

Fuel Compositions

The compounds of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the compounds of this invention in hydrocarbon fuel will range from about 50 to 2,500 parts per million (ppm) by weight, preferably about 75 to 1,000 ppm. When other deposit control additives are present, a lesser amount of the present additive may be used.

The compounds of the present invention may be formulated as a concentrate using an inert stable oleophilic (i.e., dissolves in gasoline) organic solvent boiling in the range of from about 150° F. to 400° F. (from about 65° C. to 205° C.). Preferably, an aliphatic or an aromatic hydrocarbon solvent is used, such as benzene, toluene, xylene or higher-boiling aromatics or aromatic thinners. Aliphatic alcohols containing from about 3 to 8 carbon atoms, such as isopropanol, isobutylcarbinol, n-butanol, and the like, in combination with hydrocarbon solvents are also suitable for use with the present additives. In the concentrate, the amount of the additive will generally range from about 10 to 70 weight percent, preferably about 10 to 50 weight percent, more preferably from about 20 to 40 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, hydrocarbyl poly(oxyalkylene) aminocarbamates, succinimides, or Mannich bases. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the pyridyl esters of this invention. The carrier fluid is a chemically inert hydrocarbon-soluble liquid vehicle, which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils. Such carrier fluids are described, for example, in U.S. Pat. No. 4,191,537 to Lewis, and polyesters, such as those described, for example, in U.S. Pat. Nos. 3,756,793 to Robinson and U.S. Pat. No. 5,004,478 to Vogel et al., and in European Patent Application Nos. 356,726, published Mar. 7, 1990, and 382,159, published Aug. 16, 1990.

These carrier fluids are believed to act as a carrier for the fuel additives of the present invention and to assist in removing and retarding deposits. The carrier fluid may also exhibit synergistic deposit control properties when used in combination with a pyridyl and piperidyl ester of this invention.

The carrier fluids are typically employed in amounts ranging from about 100 to 5,000 ppm by weight of the hydrocarbon fuel, preferably about 400 to 3,000 ppm of the fuel. Preferably, the ratio of carrier fluid to deposit control additive will range from about 0.5:1 to 10:1, more preferably about 1:1 to 4:1, most preferably about 2:1.

When employed in a fuel concentrate, carrier fluids will generally be present in amounts ranging from about 20 to about 60 weight percent, preferably about 30 to 50 weight percent.

PREPARATIONS AND EXAMPLES

A further understanding of the invention can be had in the following non-limiting Examples. Wherein unless expressly stated to the contrary, all temperatures and temperature ranges refer to the Centigrade system and the term "ambient" or "room temperature" refers to from about 20° C. to 25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 300 mHz, signals are assigned as singlets (s), broad singlets (bs), doublets (d), double doublets (dd), triplets (t), double triplets (dt), quartets (q), and multiplets (m), and cps refers to cycles per second.

Example 1

Preparation of Polvisobutyl Phenol

To a flask equipped with a magnetic stirrer, reflux condenser, thermometer, addition funnel and nitrogen inlet was added 203.2 grams of phenol. The phenol was warmed to 40° C. and the heat source was removed. Then, 73.5 ml of boron trifluoride etherate was added dropwise. 1040 grams of Ultravis 10 Polyisobutene (molecular weight 950, 76% methylvinylidene, available from British Petroleum) was dissolved in 1,863 ml of hexane. The polyisobutene was added to the reaction at a rate to maintain the temperature between 22° C. to 27° C. The reaction mixture was stirred for 16 hours at room temperature. Then, 400 ml of concentrated ammonium hydroxide was added, followed by 2,000 milliliters of hexane. The reaction mixture was washed with water (3×2,000 milliliters), dried over magnesium sulfate, filtered, and the solvents removed under vacuum to yield 1,056.5 grams of a crude reaction product. The crude reaction product was determined to contain 80% of the desired product by proton NMR and chromatography on silica gel eluting with hexane, followed by hexane: ethyl acetate: ethanol (93:5:2).

Example 2

Preparation of

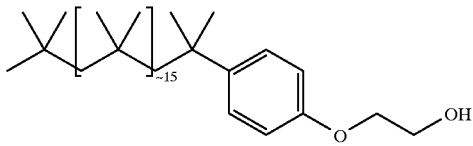

Potassium hydride (1.1 grams of a 35 weight percent dispersion of in mineral oil) and 4-polyisobutyl phenol (99.7 grams, prepared as in Example 1) were added to a flask equipped with a magnetic stirrer, reflux condenser, nitrogen inlet, and thermometer. The reaction was heated at 130° C. for one hour and then cooled to 100° C. Ethylene carbonate (8.6 grams) was added and the mixture was heated at 160° C. for 16 hours. The reaction was cooled to room temperature and 1 ml of isopropanol was added. The reaction was diluted with one liter of hexane, washed three times with water and once with brine. The organic layer was dried over anhydrous magnesium sulfate, filtered, and the solvents removed in vacuo to yield 98.0 grams of the desired alcohol as a yellow oil.

Example 3

Preparation of

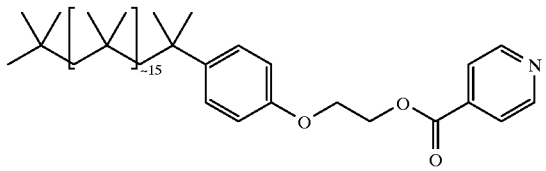

The alcohol prepared as in Example 2 (59.89 grams, 0.055 moles) was dissolved in toluene (300 ml). Isonicotinoyl chloride hydrochloride (11.71 grams, 0.066 moles) was added, followed by 4-dimethylaminopyridine (3.66 grams, 0.030 moles), and triethylamine (13 ml, 0.093 moles). The resulting mixture was refluxed with stirring under nitrogen for 24 hours. The reaction solution was washed three times with a saturated sodium bicarbonate solution and once with brine. The organic layer was dried over anhydrous magnesium sulfate, filtered, and the toluene was removed in vacuo. The resulting oil was chromatographed on silica gel eluting with hexane followed by hexane: ethyl acetate: ethanol (90:9:1) to yield 38.74 grams of the desired ester as an amber oil. IR (neat) 1737 cm$^{-1}$, $^1$H NMR (CDCl$_3$) $\delta$8.8 (AB quartet, 2H), 7.9 (AB quartet, 2H), 7.3 (AB quartet, 2H), 6.85 (AB quartet, 2H), 4.7 (t, 2H), 4.3 (t, 2H), 0.7–3.1 (m, 137 H).

Example 4

Preparation of

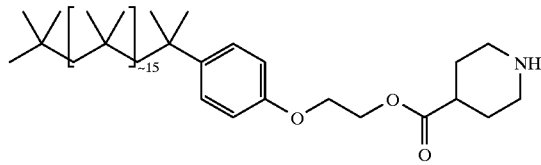

A solution of 17.26 grams of the product from Example 3 in 100 ml of toluene and 200 ml of ethyl acetate containing 2.23 grams of 10% palladium on activated carbon was hydrogenated at 50 psi for 119 hours on a Parr low-pressure hydrogenator. Solvent filtration and removal of the solvent in vacuo yielded 16.54 grams of the desired piperdine as an oil. $^1$H NMR (CDCl$_3$) $\delta$7.25 (AB quartet, 2H), 6.8 (AB quartet, 2H), 4.4 (t, 2H), 4.15 (t, 2H), 2.3–3.2 (m, 5H), 0.7–2.0 (m, 142H).

Example 5

Single-Cylinder Engine Test

The test compounds were blended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights are the weight of the deposit. A lesser amount of deposit indicates a superior additive. The operating conditions of the test were as follows: water jacket temperature 200° F.; vacuum of 12 in. Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table I.

TABLE I

| Sample[1] | Intake Valve Deposit Weight (in milligrams) |
|---|---|
| Base Fuel | 258.1 |
| Example 3 | 186.1 |
| Example 4 | 135.6 |

[1]At 50 parts per million actives (ppma) and 50 ppm of α-hydroxy-ω-4-dodecylphenoxypoly(oxypropylene) having an average of 12–13 oxypropylene units (prepared essentially as described in Example 6 of U.S. Pat. No. 4,160,648) carrier oil.

The base fuel employed in the above single-cylinder engine tests was a regular octane unleaded gasoline containing no fuel detergent. The test compounds were admixed with the base fuel to give a concentration of 50 ppma (parts per million actives) and 50 ppm of α-hydroxy-ω-4-dodecylphenoxypoly(oxypropylene) having an average of 12–13 oxypropylene units (prepared essentially as described in Example 6 of U.S. Pat. No. 4,160,648) carrier oil.

The data in Table I illustrate the significant reduction in intake valve deposits provided by the esters of the present invention (Examples 3 and 4) compared to the base fuel.

What is claimed is:

1. A compound of the formula:

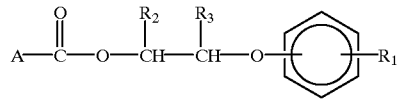

or a fuel soluble salt thereof, wherein A is selected from the group consisting of 3-pyridyl, 4-pyridyl, 3-piperidyl, and 4-piperidyl;

R$_1$ is a polyalkyl group having an average molecular weight in the range of from about 450 to 5,000; and R$_2$ and R$_3$ are independently hydrogen or lower alkyl having from about 1 to 6 carbon atoms.

2. The compound according to claim 1, wherein A is 4-pyridyl or 4-piperidyl.

3. The compound according to claim 2, wherein A is 4-piperidyl.

4. The compound according to claim 1 wherein R$_1$ is a polyalkyl group having an average molecular weight in the range of from about 500 to 3,000.

5. The compound according to claim 4 wherein R$_1$ is a polyalkyl group having an average molecular weight in the range of from about 700 to 3,000.

6. The compound according to claim 5, wherein R$_1$ is a polyalkyl group having an average molecular weight in the range of from about 900 to 2,500.

7. The compound according to claim 1, wherein R$_1$ is a polyalkyl group derived from polypropylene, polybutene, or a polyalphaolefin oligomer of 1-octene or 1-decene.

8. The compound according to claim 7 wherein R$_1$ is a polyalkyl group derived from polyisobutene.

9. The compound according to claim 8 wherein the polyisobutene contains at least about 20% of a methylvinylidene isomer.

10. The compound according to claim 1, wherein one of R$_2$ and R$_3$ is hydrogen or lower alkyl of from about 1 to 4 carbon atoms, and the other is hydrogen.

11. The compound according to claim 10, wherein one of $R_2$ and $R_3$ is hydrogen, methyl or ethyl, and the other is hydrogen.

12. The compound according to claim 11, wherein $R_2$ is hydrogen, methyl or ethyl, and $R_3$ is hydrogen.

13. A fuel composition comprising a major amount of hydrocarbons boiling in the gasoline or diesel range and an effective deposit-controlling amount of a compound of the formula:

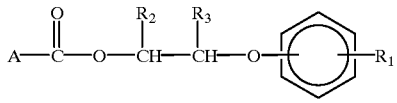

or a fuel soluble salt thereof, wherein A is selected from the group consisting of 3-pyridyl, 4-pyridyl, 3-piperidyl, and 4-piperidyl;

R$_1$ is a polyalkyl group having an average molecular weight in the range of from about 450 to 5,000; and R$_2$ and R$_3$ are independently hydrogen or lower alkyl having from about 1 to 6 carbon atoms.

14. The fuel composition according to claim 13, wherein A is 4-pyridyl or 4-piperidyl.

15. The fuel composition according to claim 14, wherein A is 4-piperidyl.

16. The fuel composition according to claim 13, wherein R$_1$ is a polyalkyl group having an average molecular weight in the range of from about 500 to 3,000.

17. The fuel composition according to claim 16, wherein R$_1$ is a polyalkyl group having an average molecular weight in the range of from about 700 to 3,000.

18. The fuel composition according to claim 17, wherein R$_1$ is a polyalkyl group having an average molecular weight in the range of from about 900 to 2,500.

19. The fuel composition according to claim 13, wherein R$_1$ is a polyalkyl group derived from polypropylene, polybutene, or a polyalphaolefin oligomer of 1-octene or 1-decene.

20. The fuel composition according to claim 19, wherein R$_1$ is a polyalkyl group derived from polyisobutene.

21. The fuel composition according to claim 20, wherein the polyisobutene contains at least about 20% of a methylvinylidene isomer.

22. The fuel composition according to claim 13, wherein one of R$_2$ and R$_3$ is hydrogen or lower alkyl of from about 1 to 4 carbon atoms, and the other is hydrogen.

23. The fuel composition according to claim 22, wherein one of R$_2$ and R$_3$ is hydrogen, methyl or ethyl, and the other is hydrogen.

24. The fuel composition according to claim 23, wherein R$_2$ is hydrogen, methyl or ethyl, and R$_3$ is hydrogen.

25. The fuel composition according to claim 13, wherein the composition contains from about 50 to 2,000 parts per million by weight of said compound.

26. The fuel composition according to claim 25, where the composition further contains from about 100 to 5,000 parts per million by weight of a fuel-soluble, nonvolatile carrier fluid.

27. A fuel concentrate comprising an inert stable oleophilic organic solvent boiling in the range of from about 150° F. to 400° F. and from about 10 to 70 weight percent of a compound of the formula:

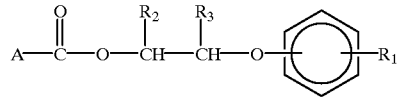

or a fuel soluble salt thereof, wherein A is selected from the group consisting of 3-pyridyl, 4-pyridyl, 3-piperidyl, and 4-piperidyl;

R$_1$ is a polyalkyl group having an average molecular weight in the range of from about 450 to 5,000; and R$_2$ and R$_3$ are independently hydrogen or lower alkyl having from about 1 to 6 carbon atoms.

28. The fuel concentrate according to claim 27, wherein A is 4-pyridyl or 4-piperidyl.

29. The fuel concentrate according to claim 28, wherein A is 4-piperidyl.

30. The fuel concentrate according to claim 27, wherein R$_1$ is a polyalkyl group having an average molecular weight in the range of from about 500 to 3,000.

31. The fuel concentrate according to claim 30, wherein R$_1$ is a polyalkyl group having an average molecular weight in the range of from about 700 to 3,000.

32. The fuel concentrate according to claim 31, wherein R$_1$ is a polyalkyl group having an average molecular weight in the range of from about 900 to 2,500.

33. The fuel concentrate according to claim 27, wherein R$_1$ is a polyalkyl group derived from polypropylene, polybutene, or a polyalphaolefin oligomer of 1-octene or 1-decene.

34. The fuel concentrate according to claim 33, wherein R$_1$ is a polyalkyl group derived from polyisobutene.

35. The fuel concentrate according to claim 34, wherein the polyisobutene contains at least about 20% of a methylvinylidene isomer.

36. The fuel concentrate according to claim 27, wherein one of R$_2$ and R$_3$ is hydrogen or lower alkyl of from about 1 to 4 carbon atoms, and the other is hydrogen.

37. The fuel concentrate according to claim 36, wherein one of R$_2$ and R$_3$ is hydrogen, methyl or ethyl, and the other is hydrogen.

38. The fuel concentrate according to claim 37, wherein R$_2$ is hydrogen, methyl or ethyl, and R$_3$ is hydrogen.

39. The fuel concentrate according to claim 27, wherein the fuel concentrate further contains from about 20 to 60 weight percent of a fuel-soluble, nonvolatile carrier fluid.

* * * * *